(12) United States Patent
Yamakoshi et al.

(10) Patent No.: US 6,694,821 B2
(45) Date of Patent: Feb. 24, 2004

(54) CUFF OF WRIST-MOUNT BLOOD PRESSURE MONITOR

(75) Inventors: Ken-ichi Yamakoshi, Kanazawa (JP); Shojiro Oku, Kyoto (JP); Takahide Tanaka, Kyoto (JP); Yoshihiko Sano, Kyoto (JP); Hiroyuki Kato, Kyoto (JP)

(73) Assignee: Omron Corporation, Kyoto (JP)

( * ) Notice: Subject to any disclaimer, the term of this patent is extended or adjusted under 35 U.S.C. 154(b) by 0 days.

(21) Appl. No.: 10/135,847

(22) Filed: May 1, 2002

(65) Prior Publication Data

US 2002/0170359 A1 Nov. 21, 2002

(30) Foreign Application Priority Data

May 7, 2001 (JP) ........................................ 2001/135955

(51) Int. Cl.⁷ ................................................. G01L 7/00
(52) U.S. Cl. .......................... 73/756; 600/490; 600/500; 600/485; 600/492
(58) Field of Search ................................. 600/300, 500, 600/485, 494, 490, 499, 492, 503; 73/756

(56) References Cited

U.S. PATENT DOCUMENTS

| 5,511,551 | A | | 4/1996 | Sano et al. |
|---|---|---|---|---|
| 5,997,495 | A | * | 12/1999 | Cook et al. ................. 602/63 |
| 6,231,517 | B1 | * | 5/2001 | Forstner ....................... 600/485 |
| 6,315,734 | B1 | * | 11/2001 | Nunome ....................... 600/500 |
| 6,336,901 | B1 | | 1/2002 | Itonaga et al. |
| 6,514,212 | B1 | | 2/2003 | Ide et al. |
| 2002/0026121 | A1 | * | 2/2002 | Kan ............................ 600/500 |

FOREIGN PATENT DOCUMENTS

| EP | 0 615 722 A1 | 9/1994 |
|---|---|---|
| EP | 1 075 846 A2 | 2/2001 |
| EP | 1 256 313 A3 | 11/2002 |
| FR | 2568464 A1 | 2/1986 |
| JP | 0172726 A2 | 6/2000 |
| JP | 2000-229070 A | 8/2000 |
| JP | 2000-350706 | 12/2000 |

* cited by examiner

Primary Examiner—Andrew H. Hirshfeld
Assistant Examiner—Marissa Ferguson
(74) Attorney, Agent, or Firm—Morrison & Foerster LLP

(57) ABSTRACT

A cuff of a wrist-mount blood pressure monitor capable of oppressing an artery of the wrist securely without having effects of muscle, tendon or bone existing in the wrist area is presented. This cuff 10 of a wrist-mount blood pressure monitor comprises a first air bag 14A as a first inflatable portion, and a second air bag 16A as a second inflatable region disposed between the first inflatable portion 14A and the wrist, being made of a material of a higher stretchability than the material for the first air bag 14A.

9 Claims, 10 Drawing Sheets

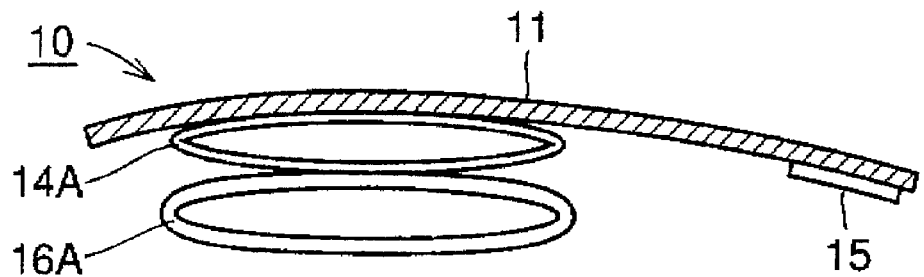
10: Cuff of wrist-mount blood pressure monitor  11: Belt
14A: First air bag  15: Fastener  16A: Second air bag
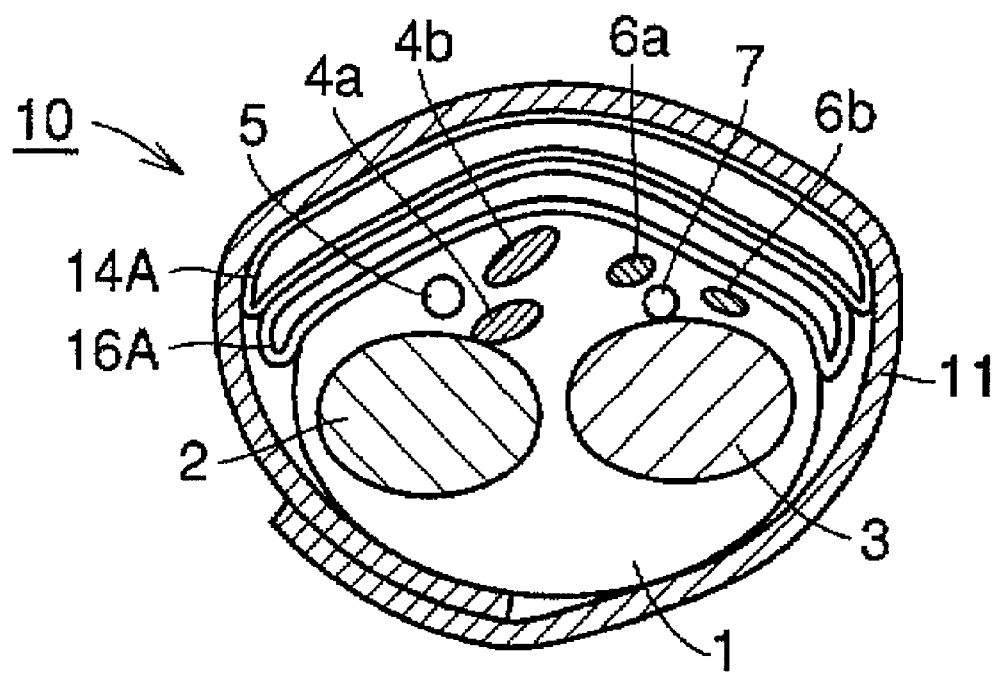

[Fig. 3]
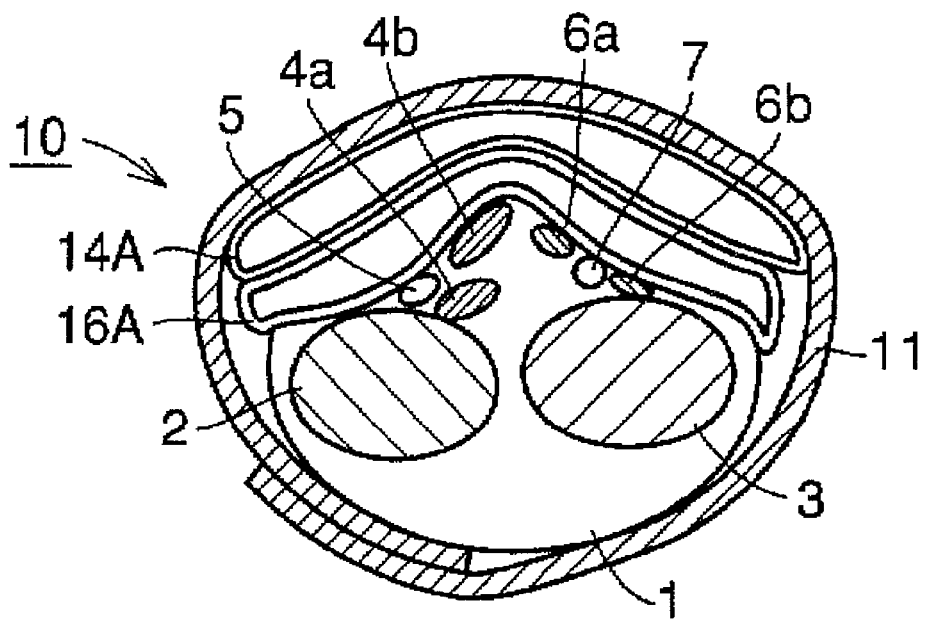
[Fig. 4]
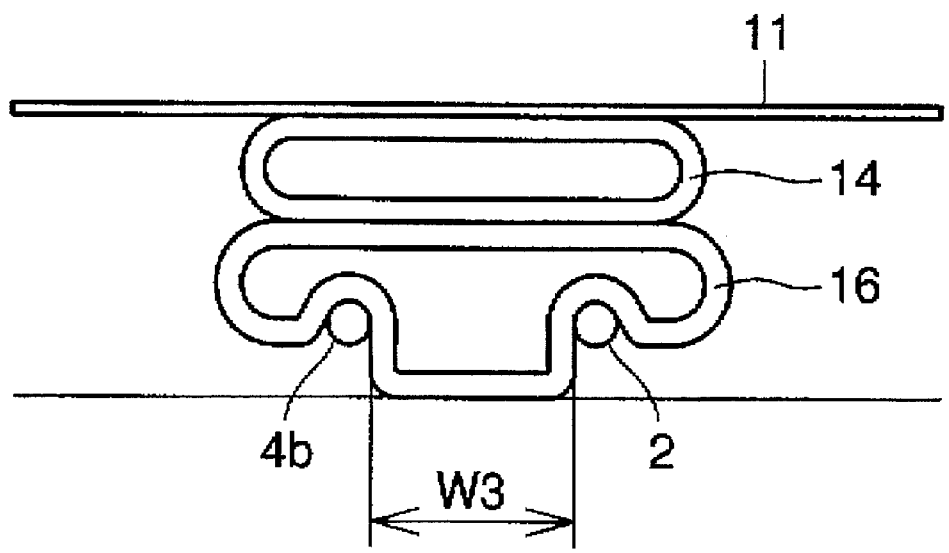

[Fig. 5]
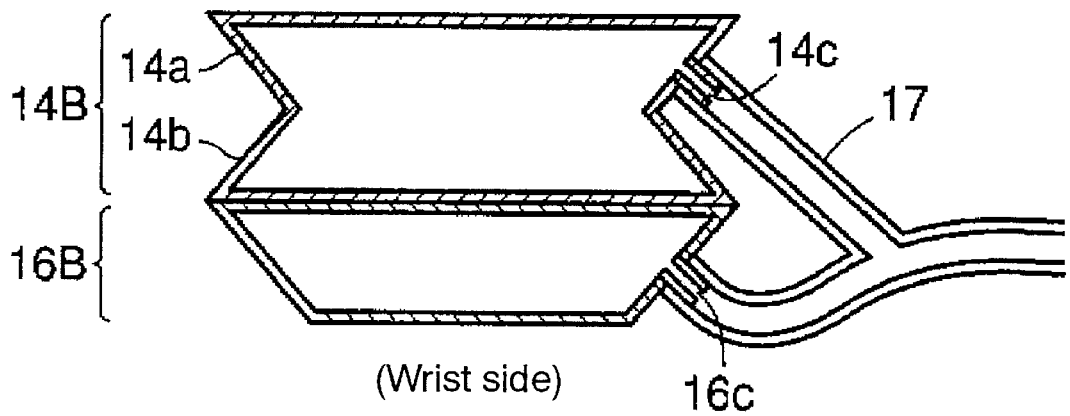
14B: First air bag  16B: Second air bag
[Fig. 6]
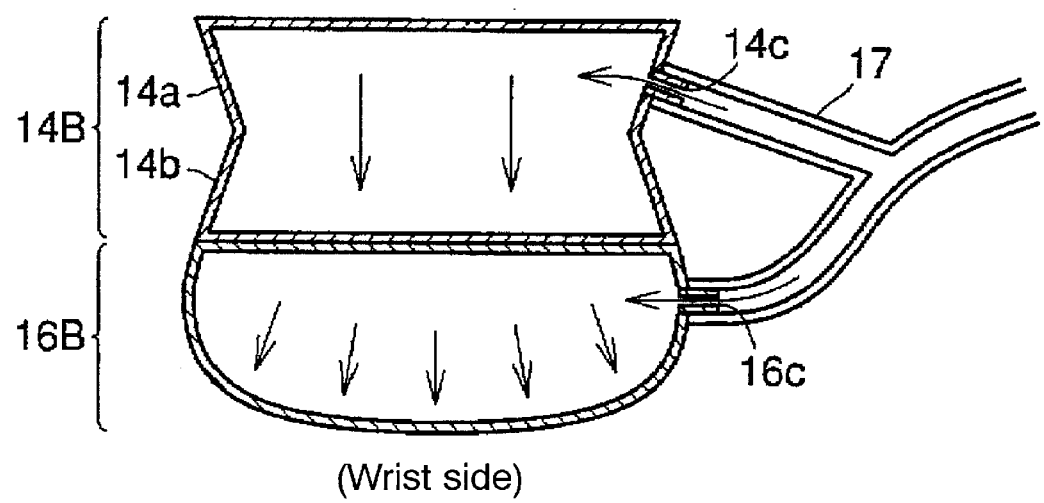

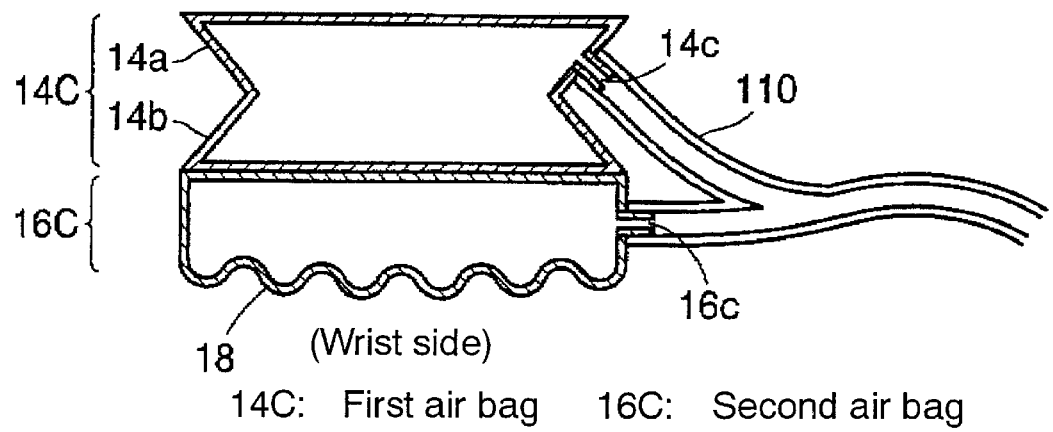
[Fig. 7]
14C: First air bag   16C: Second air bag
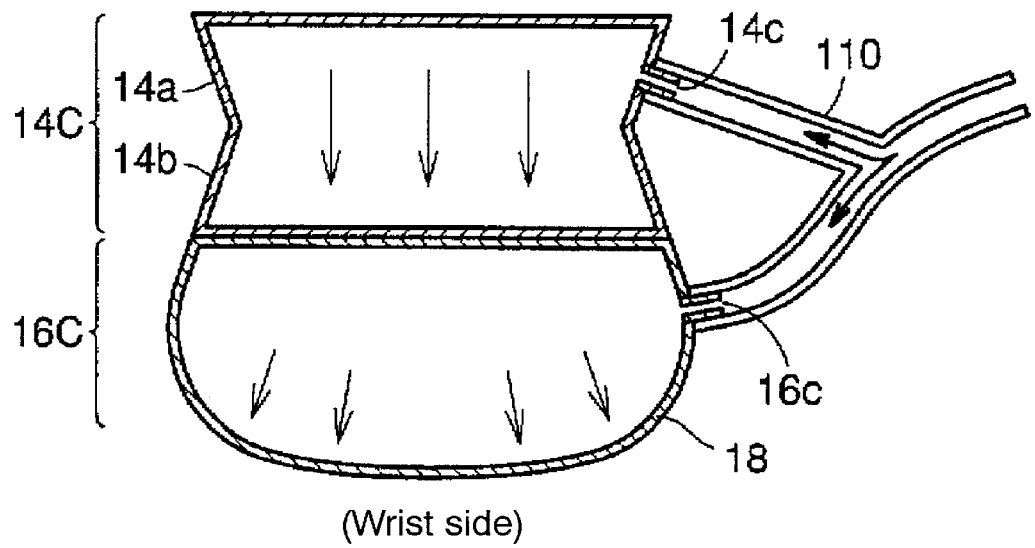
[Fig. 8]

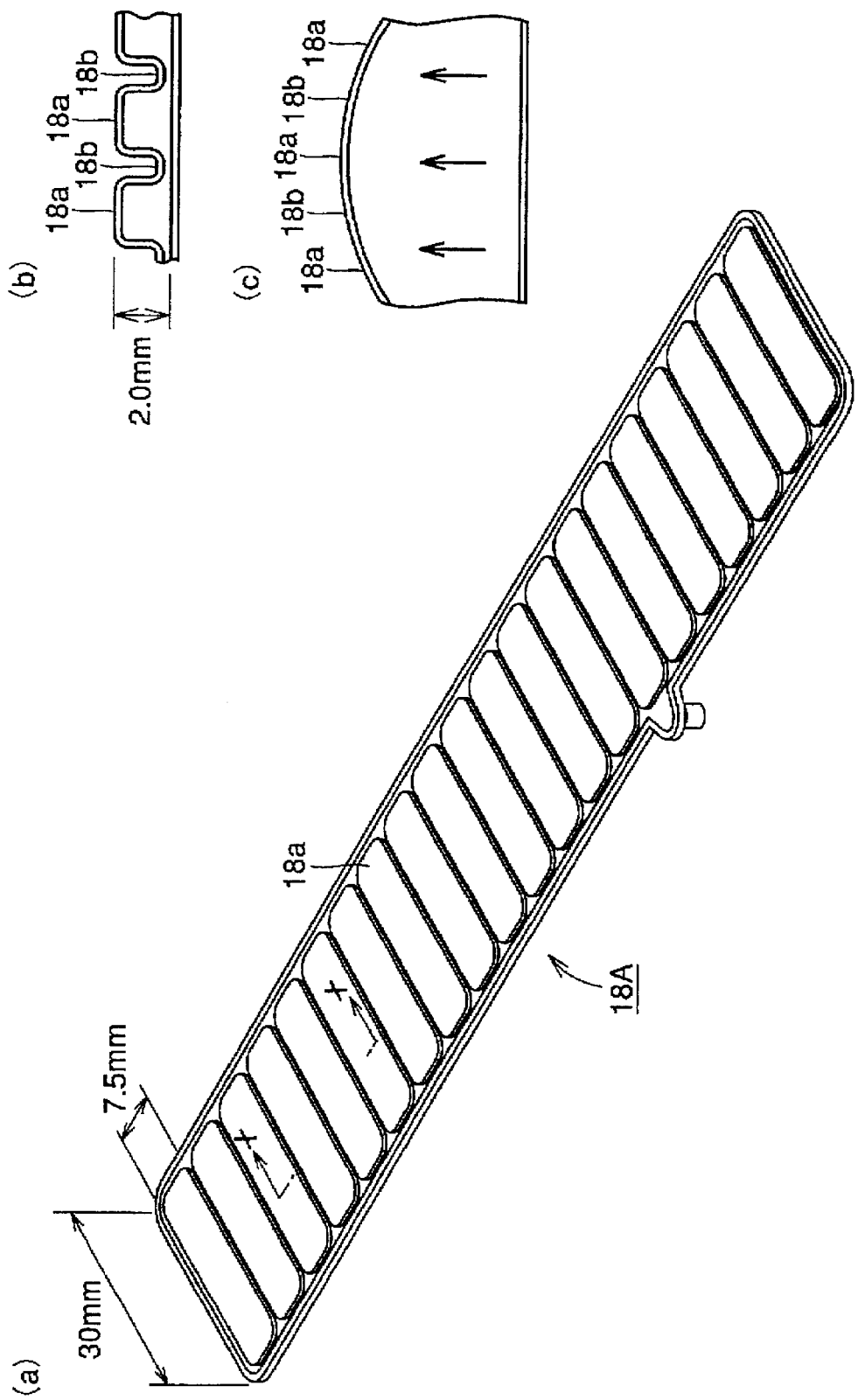
[Fig. 9]

[Fig. 10]
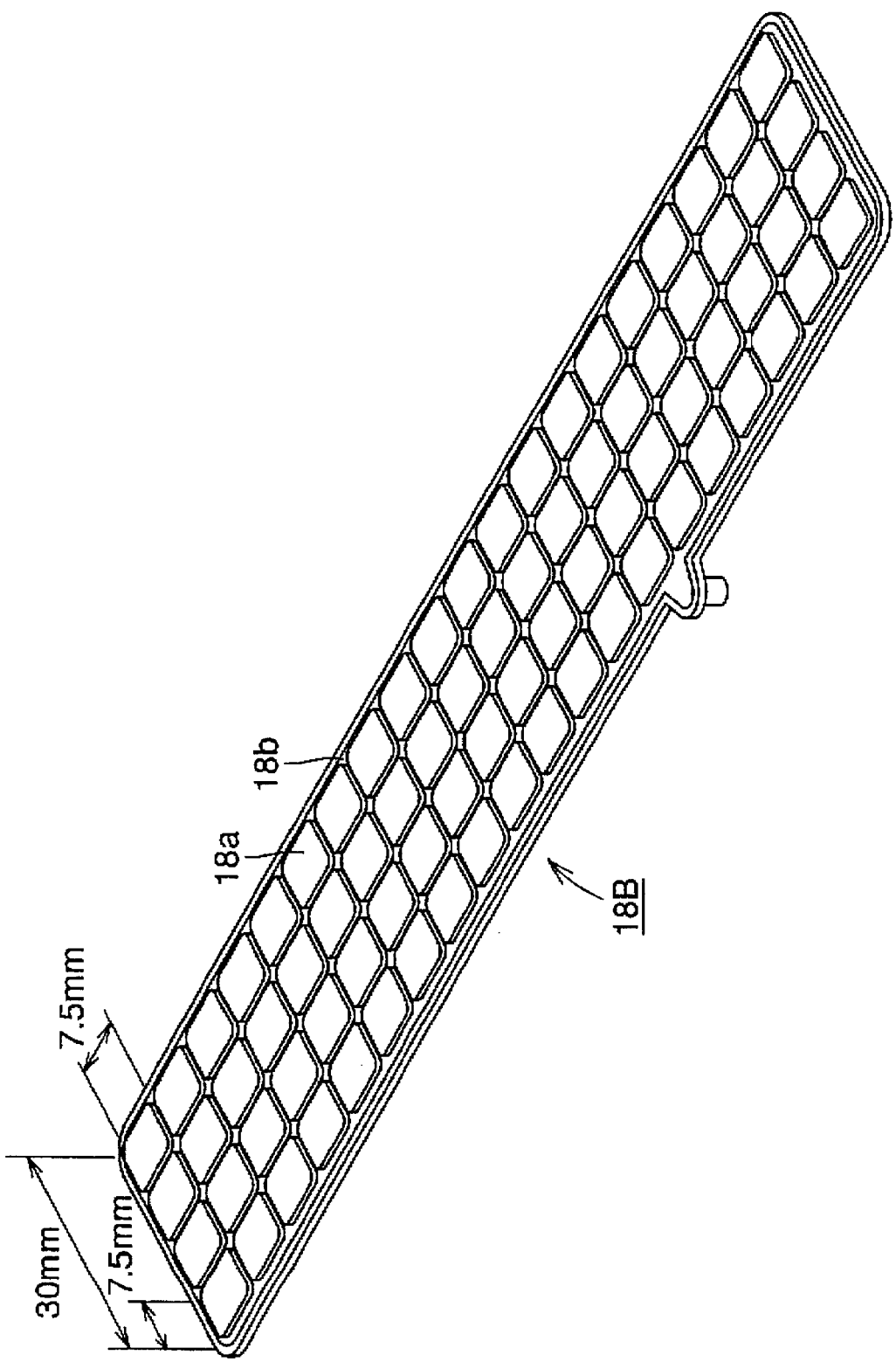

[Fig. 11]
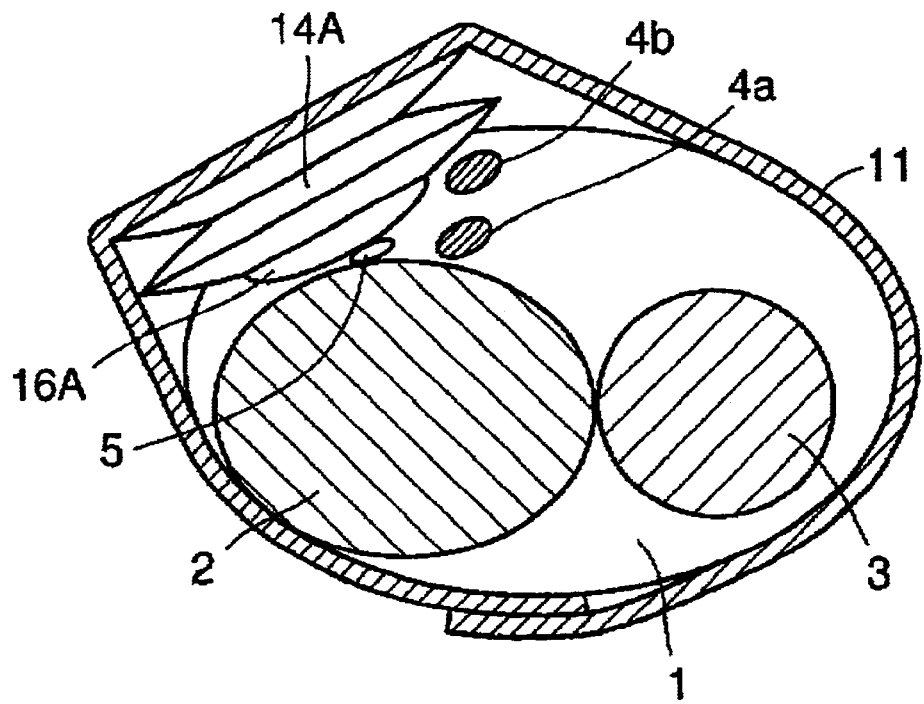
[Fig. 12]
Prior Art
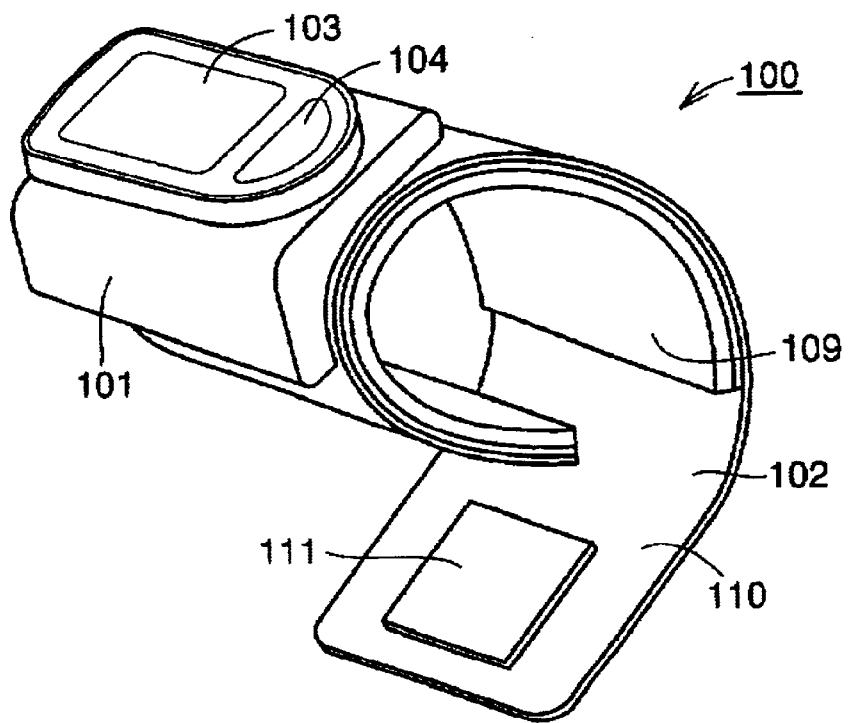

[Fig. 13]
Prior Art
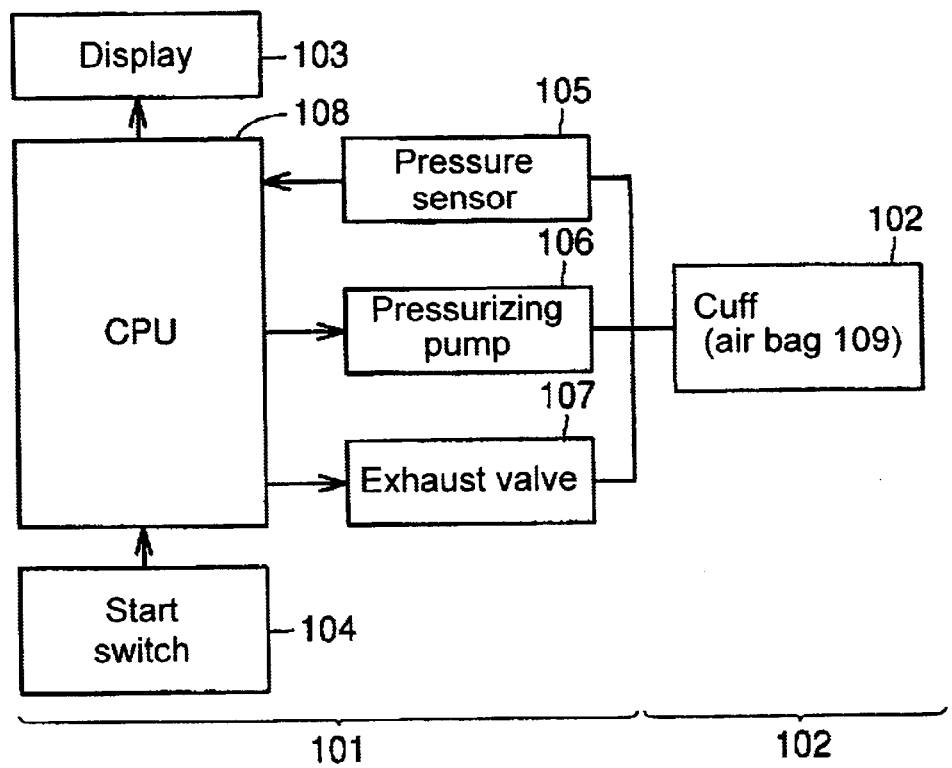
[Fig. 14]
Prior Art
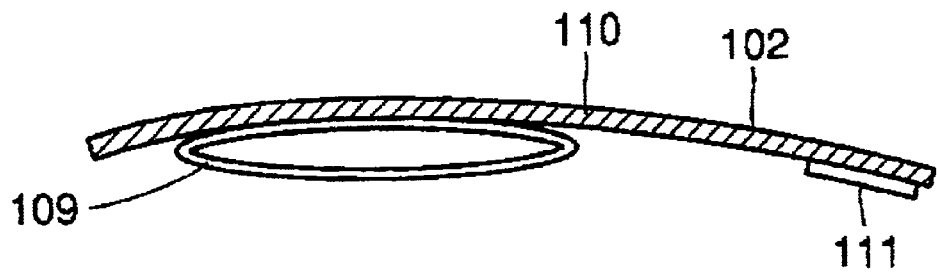

[Fig. 15]
Prior Art
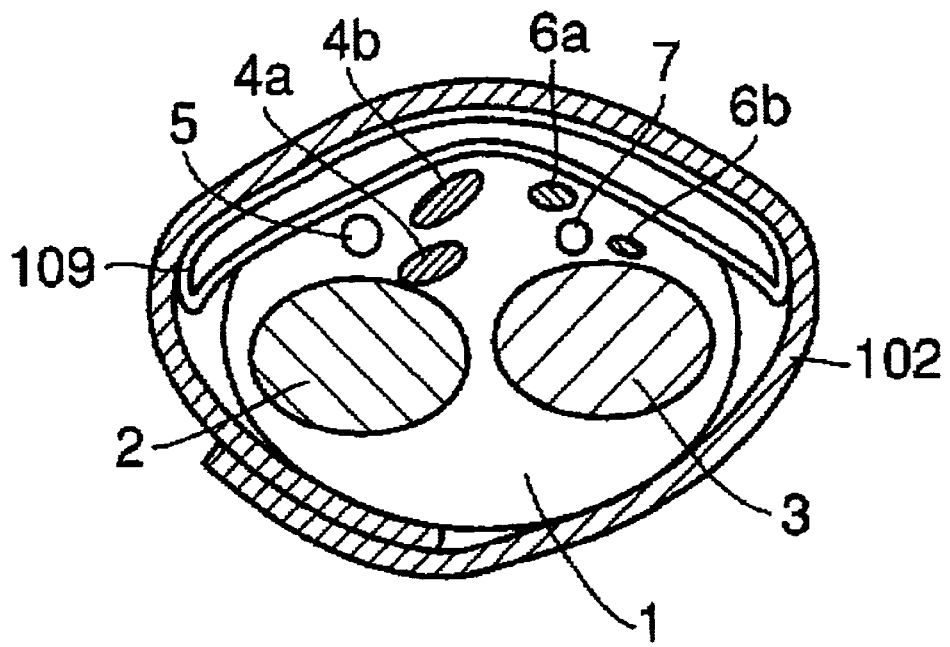
[Fig. 16]
Prior Art
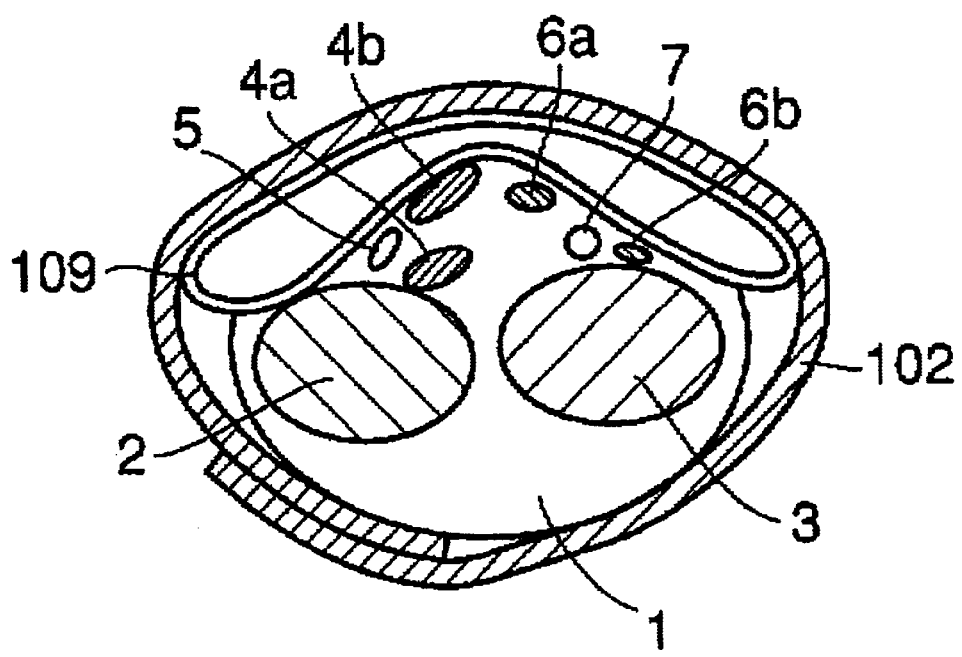

[Fig. 17]
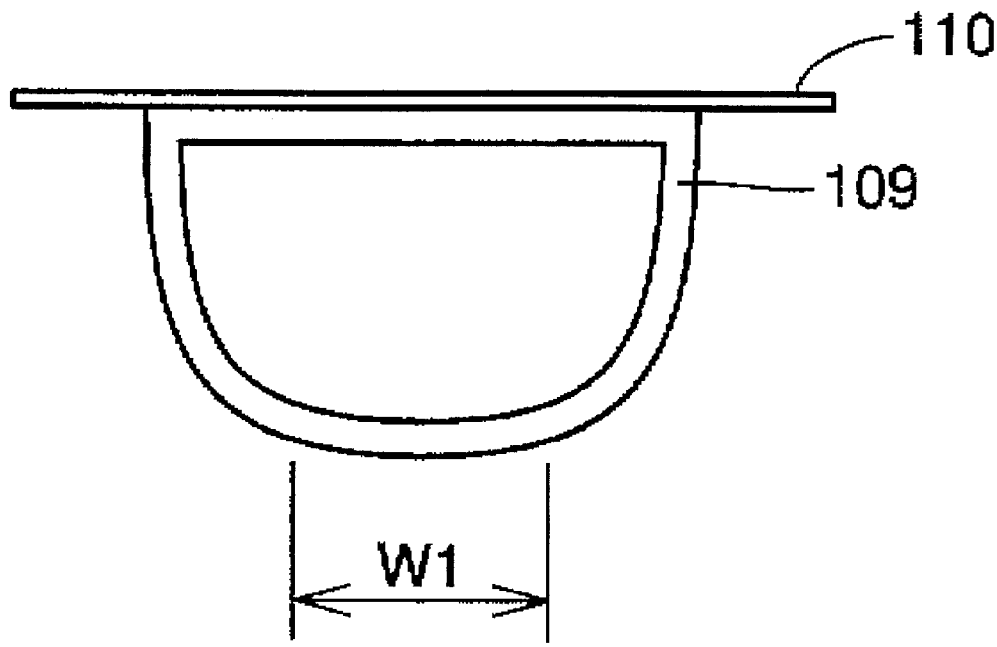
[Fig. 18]
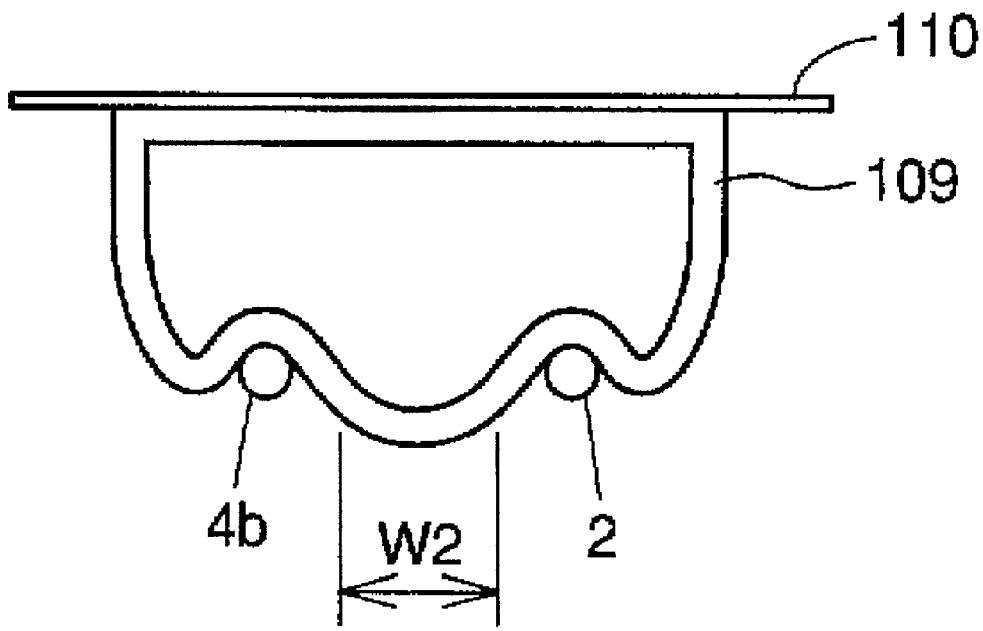

CUFF OF WRIST-MOUNT BLOOD PRESSURE MONITOR

BACKGROUND OF THE INVENTION

1. Field of the Invention

The present invention relates to a cuff of a blood pressure monitor for measuring the blood pressure as being mounted on the body of a subject, and more particularly relates to a structure of the cuff of a wrist-mount blood pressure monitor used in a wrist-mount blood pressure monitor for measuring the blood pressure on the wrist.

2. Description of the Related Art

Recently, importance of self-control of blood pressure has recognized, and the wrist-mount blood pressure monitor capable of measuring more easily than the brachial type is widely used at home as a household blood pressure monitor. A schematic configuration of a conventional wrist-mount blood pressure monitor 100 is explained by referring to FIG. 12 and FIG. 13. FIG. 12 is a general perspective view showing the appearance of the wrist-mount blood pressure monitor 100, and FIG. 13 is a block diagram showing an internal structure of the wrist-mount blood pressure monitor 100. Referring to both diagrams, the wrist-mount blood pressure monitor 100 comprises a main body 101 incorporating a control device for measuring the blood pressure, and a cuff 102 of a wrist-mount blood pressure monitor which the main body 101 is attached.

A display 103 and a start switch 104 are provided on the outer surface of the main body 101, and a pressure sensor 105, a pressurizing pump 106, an exhaust valve 107, and a CPU 108 for controlling these devices are provided in its inside.

The cuff 102 of wrist-mount blood pressure monitor comprises an air bag 109 for collecting the air sent out from the pressurizing pump 106 and oppressing an artery of the wrist, a band 110 having the air bag 109 disposed at its inner side for mounting on the wrist, and a fastener 111 for winding and fixing the band 110 on the wrist.

Measurement of blood pressure by using the wrist-mount blood pressure monitor 100 having such configuration is explained by referring to FIG. 14 to FIG. 16. In FIG. 14 to FIG. 16, for the sake of convenience, only the cuff 102 of the wrist-mount blood pressure monitor is shown, and the main body 101 is not shown. FIG. 14 is a schematic sectional view of the cuff 102 of the wrist-mount blood pressure monitor along the longitudinal direction before mounting on the wrist, and air is not supplied into the air bag 109 yet. FIG. 15 is a sectional diagram showing a deflated state of the cuff 102 of the wrist-mount blood pressure monitor mounted on the wrist 1. FIG. 16 is a sectional view showing an inflated state of the cuff 102 of the wrist-mount blood pressure monitor mounted on the wrist 1.

The cuff 102 of the wrist-mount blood pressure monitor shown in FIG. 14 is fixed by using the band 110 so that the air bag 109 comes to a position confronting the radial artery 5 and ulnar artery 7 of the wrist 1. Herein, the principal constituents of the wrist 1 include, as shown in FIG. 15, the radius 2 positioned at the thumb side, the ulna 3 positioned as the little finger side, the deep flexor digital tendon 4a and palmar long flexor tendon 4b positioned near the radius 2, the radial artery 5, the superficial flexor digital tendon 6a and ulnar carpal tendon 6b positioned near the ulna 3, and the ulnar artery 7.

When the cuff 102 of the wrist-mount blood pressure monitor is completely mounted on the wrist 1, by supplying air from the pressurizing pump 106 into the air bag 109 as shown in FIG. 16, the radial artery 5 or the ulnar artery 7 (or both) of the wrist 1 is oppressed, and the exhaust valve 107 is released, and in the process of discharging air from the air bag 109, the pressure in the air bag 109 is measured by the blood pressure sensor 105, and the blood pressure measurement data is obtained.

The wrist-mount blood pressure monitor is said to be inferior in precision to the brachial type blood pressure monitor. One of the causes is lack of oppression force on the artery of the wrist. Lack of oppression force on the artery means that the pressure of the vascular inner wall to be measure (hereinafter called vascular inner wall pressure) is smaller as compared with the air bag inner pressure. When the vascular inner wall pressure and air bag inner pressure are equal, by measuring the air bag inner pressure, an accurate vascular inner wall pressure is obtained, so that an accurate blood pressure can be measured.

However, when the oppression force is insufficient, the air bag inner pressure becomes higher than the vascular inner wall pressure, and the air bag inner pressure is directly measured as the blood pressure, so that a higher blood pressure than the actual pressure is measured. One of the causes of such lack of oppression force is lack of oppression width (hereinafter cuff width) in the wrist by the air bag.

The guideline of cuff width of brachial type blood pressure monitor is specified by AHA (American Heart Association), but there is no guideline for the cuff width of wrist-mount blood pressure monitor. Accordingly, the definition of cuff width of the brachial type blood pressure monitor (width of specific multiple of diameter of applicable brachial girth) is directly applied to the wrist. At the present, the cuff width of wrist-mount blood pressure monitor is set at about 50 to 60 mm. If the cuff width of the wrist-mount blood pressure monitor is determined according to this definition, lack of oppression force occurs. One of the causes is that the wrist contains many muscles and tendons not existing in the brachium, and the bones are present relatively near the cuticle, and the oppression of artery by the air bag is impeded.

As shown in a sectional view in FIG. 16, a sufficient air is supplied in the air bag 109, and the air bag 109 is inflated toward the wrist 1 side. However, due to the presence of the radius 2 and palmar long flexor tendon 4b, the inflation of the air bag 109 is impeded, and the radial artery 5 is not oppressed sufficiently, and also the inflation of the air bag 109 is impeded by the presence of the superficial flexor digital tendon 6a and ulnar carpal tendon 6b, and the ulnar artery 7 is not sufficiently oppressed.

If the oppression of artery by the air bag 109 is not impeded at all, as schematically shown in FIG. 17, a specified cuff width W1 can be obtained by sufficiently inflating the air bag 109, but in the presence of the radius 2, palmar long flexor tendon 4b, and others, as schematically shown in FIG. 18, inflation of the air bag 109 is impeded by the presence of the radius 2, palmar long flexor tendon 4b, and others, and hence the cuff width W2 is insufficient.

It is hence a primary object of the invention to present a cuff of wrist-mount blood pressure monitor capable of oppressing the artery positioned at the wrist securely without having effects of muscle, tendon and bone existing in the wrist area.

SUMMARY OF THE INVENTION

The cuff of a wrist-mount blood pressure monitor according to the invention comprises an inflatable bag receiving a predetermined amount of a fluid for pressurizing an artery of the wrist, and mounting means for mounting the inflatable bag on the wrist, in which the inflatable bag includes a first inflatable portion, and a second inflatable portion disposed between the first inflatable portion and the wrist, being made of a material having a higher stretchability than the material of the first inflatable portion.

In this configuration, when a fluid is supplied into the inflatable bag, both the first inflatable portion and second inflatable portion are inflated by the supply of the fluid. Since the second inflatable portion is made of a material having a higher stretchability than the material of the first inflatable portion, a specified pressure to the wrist side is assured by inflation of the first inflatable portion. Moreover, the second inflatable portion is inflated in a state of tight contact with the wrist, the second inflatable portion flexibly intrudes into the tendons and bones, so that the second inflatable portion may intrude into the spaces between a tendon and a tendon, between a tendon and a bone, or between a bone and a bone.

Accordingly, regardless of the presence of muscle, tendon or bone in the wrist, it is possible to sufficiently apply a pressure to the artery of the wrist since the pressure from the first inflatable portion is applied to the wrist with which the second inflatable portion comes into contact. As a result, insufficient pressurizing force can be improved, so that it is possible to measure the blood pressure with good accuracy even in a wrist-mount blood pressure monitor.

Owing to these features, as mentioned above, by inflation of the first inflatable portion, a specified pressure to the wrist side is assured, and the second inflatable portion is inflated in a state of tight contact with the wrist, so that the second inflatable portion may flexible intrude into the muscles, tendons and bones.

Further preferably, the shape of the second inflatable portion at the wrist side is formed of extruding portions and dent portions. By the shape of extruding portions and dent portions, a higher expanding and contracting property may be obtained, and intrusion of the second inflatable portion into the muscles, tendons and tone when inflated can be realized more securely.

BRIEF DESCRIPTION OF THE DRAWINGS

FIG. 1 is a schematic view of a sectional structure of a cuff 10 of a wrist-mount blood pressure monitor along the longitudinal direction before mounting on the wrist in a preferred embodiment of the invention.

FIG. 2 is a sectional view showing the cuff 10 of a wrist-mount blood pressure monitor being mounted on the wrist 1.

FIG. 3 is a sectional view showing a state of pressing the wrist 1 by the cuff 10 of a wrist-mount blood pressure monitor.

FIG. 4 is a schematic view showing the principle of oppression of the wrist by using the cuff 10 of a wrist-mount blood pressure monitor.

FIG. 5 is a sectional view showing a structure at the time of deflation of first air bag 14B and second air bag 16B in embodiment 1.

FIG. 6 is a sectional view showing a structure at the time of inflation of first air bag 14B and second air bag 16B in embodiment 1.

FIG. 7 is a sectional view showing a structure at the time of deflation of first air bag 14C and second air bag 16C in embodiment 2.

FIG. 8 is a sectional view showing a structure at the time of inflation of first air bag 14C and second air bag 16C in embodiment 2.

FIG. 9 is a general perspective view (a), a sectional arrow view of X—X (b), and a sectional view in inflated state (c), showing a first undulated shape at the wrist 1 side of the second air bag 16C.

FIG. 10 is a general perspective view showing a second undulated shape at the wrist 1 side of the second air bag 16C.

FIG. 11 is a sectional view when the cuff 10 of a wrist-mount blood pressure monitor is applied in a structure for oppressing only the vicinity of the radial pedicular process.

FIG. 12 is a general perspective view showing a structure of conventional wrist-mount blood pressure monitor 100.

FIG. 13 is a block diagram showing an internal structure of conventional wrist-mount blood pressure monitor 100.

FIG. 14 is a sectional structural view of cuff 102 of a wrist-mount blood pressure monitor along the longitudinal direction before mounting on the wrist.

FIG. 15 is a sectional view in deflated state showing a state of cuff 102 of a wrist-mount blood pressure monitor mounted on the wrist 1.

FIG. 16 is a sectional view in inflated state showing a state of cuff 102 of a wrist-mount blood pressure monitor mounted on the wrist 1.

FIG. 17 is a schematic diagram showing an ideal state of oppression of the wrist by using the cuff of a wrist-mount blood pressure monitor.

FIG. 18 is a schematic diagram showing problems of oppression of the wrist by using the cuff of a wrist-mount blood pressure monitor.

DESCRIPTION OF THE PREFERRED EMBODIMENTS

Referring to the drawings, preferred embodiments of the invention of the cuff of a wrist-mount blood pressure monitor are explained. The basic structure of the wrist-mount blood pressure monitor using the cuff of wrist-mount blood pressure monitor in the embodiments is same as that of the conventional wrist-mount blood pressure monitor 100 explained in FIG. 12, and the detailed description is omitted, and only the features of the structure of the cuff of wrist-mount blood pressure monitor of the invention are explained below.

First, the structure of the cuff of wrist-mount blood pressure monitor based on the invention and its principle of oppressing the wrist are explained below while referring to FIG. 1 to FIG. 4. FIG. 1 is a schematic view of a sectional structure of a cuff 10 of a wrist-mount blood pressure monitor along the longitudinal direction before mounting on the wrist in a preferred embodiment of the invention, FIG. 2 is a sectional view showing the cuff 10 of a wrist-mount blood pressure monitor being mounted on the wrist 1, FIG. 3 is a sectional view showing a state of pressing the wrist 1 by the cuff 10 of a wrist-mount blood pressure monitor, and FIG. 4 is a schematic view showing the principle of oppression of the wrist by using the cuff 10 of a wrist-mount blood pressure monitor.

(Configuration)

First, referring to FIG. 1, the configuration of the cuff of a wrist-mount blood pressure monitor is explained. This cuff 10 of a wrist-mount blood pressure monitor comprises a first air bag 14A as a first inflatable portion used for collecting the air sent out from a pressurizing pump and oppressing an artery of the wrist, and a second air bag 16A as a second inflatable portion disposed between the first air bag 14A and the wrist, being made of a material of a higher stretchability than the material of the first air bag 14A. A band 11 is mounting means for mounting the first air bag 14A and second air bag 16A on the wrist, and a fastener 15 is used for winding around and fixing the band 11 on the wrist. In FIG. 1, air is not supplied into the air bags yet.

(Principle of Oppression on Wrist)

Secondly, the principle of oppression on the wrist by using the cuff 10 of a wrist-mount blood pressure monitor is explained by referring to FIG. 2 to FIG. 4. Referring to FIG. 2, by using the band 11, the first air bag 14A and second air bag 16A are fixed to the positions confronting the radial artery 5 and ulnar artery 7 of the wrist 1. The constituents of the wrist 1 are same as explained in FIG. 15, and same reference numerals are given and detailed description is omitted.

Next, referring to FIG. 3, when air is supplied, the first air bag 14A is inflated toward the wrist 1 side, and further the second air bag 16A, when air is supplied, is inflated to intrude mainly into the tendons or bones of the wrist 1.

Explaining in further detail, by inflation of the second air bag 16A, the second air bag 16A intrudes into the radius 2 and palmar long flexor tendon 4b. As a result, the second air bag 16A gets into the space between the radius 2 and palmar long flexor tendon 4b, and the radial artery 5 is sufficiently oppressed by the second air bag 16A. Also by inflation of the second air bag 16A, the second air bag 16A intrudes into the superficial flexor digital tendon 6a and ulnar carpal tendon 6b. As a result, the second air bag 16A gets into the space between the superficial flexor digital tendon 6a and ulnar carpal tendon 6b, so that the ulnar artery 7 is sufficiently oppressed by the second air bag 16A.

As shown in FIG. 4, when air is supplied into the first air bag 14A and second air bag 16A, both the first air bag 14A and second air bag 16A are inflated by supply of fluid, but since the second air bag 16A is made of a material of a higher stretchability than the material of the first air bag 14A, by inflation of the first air bag 14A, a specified pressure to the wrist 1 side is maintained. In a state in tight contact with the wrist 1, the second air bag 16A is inflated, and the second air bag 16A flexibly intrudes into the tendons or bones, so that the second air bag 16A gets into the space between the radius 2 and palmar long flexor tendon 4b, and hence the pressure from the first air bag 14A is applied to the wrist 1 which is kept in contact with the second air bag 16A regardless of the presence of the radius 2 and palmar long flexor tendon 4b of the wrist 1. Similarly, the second air bag 16A gets into the space between the superficial flexor digital tendon 6a and ulnar carpal tendon 6b. As a result, a sufficient cuff width W3 can be obtained.

From the viewpoint of intrusion of the air bags into the tendons and bones, the air bags may be made of stretchable materials only. However, in the case of using air bags made of stretchable materials only, sufficient pressure is not applied in the direction for oppressing the wrist, but the air bags are largely inflated in the lateral direction, and the wrist cannot be oppressed sufficiently. Therefore, as mentioned above, it is important to combine the first air bag 14A as the first inflatable portion, and the second air bag 16A as the second inflatable portion made of a material of higher stretchability than the first air bag 14A.

(Embodiment 1)

A configuration of exemplary embodiment 1 on the basis of the above principle of oppression is explained by referring to FIG. 5 and FIG. 6. FIG. 5 shows only the air bags of the cuff 10 of wrist-mount blood pressure monitor in a deflated state before supply of air, and FIG. 6 shows an inflated state after supply of air.

As shown in FIG. 5, the structure comprises a first air bag 14B as a first inflatable portion, and a second air bag 16B as a second inflatable portion positioned between the first air bag 14B and the wrist, being made of a material of a higher stretchability than the material of the first air bag 14B. A specific material of the first air bag 14B is vinyl chloride (a film thickness of about 0.3 mm). Other material usable for the first airbag 14B includes EVA (vinyl acetate; a film thickness of about 0.3 mm), and urethane (a film thickness of about 0.3 mm).

To encourage inflation to the wrist side, a taper is formed of side walls 14a, 14b (accordion structure). When deflated, the thickness of the first air bag 14B is about 1.2 mm.

Specific materials for the second air bag 16B include thin films of silicone and latex, and the film thickness is about 0.3 mm. Other materials for the second air bag 16B include silicone and latex.

In the first air bag 14B and second air bag 16B, air feed pipes 14c, 16c are provided, and a common air feed tube 17 is coupled to equalize the air pressure between the first air bag 14B and second air bag 16B.

In the configuration above, when air is fed into the first air bag 14B and second air bag 16B, as shown in FIG. 6, since a taper is formed in the first air bag 14B, it is inflated mainly in a direction of oppressing the wrist. On the other hand, the second air bag 16B is inflated in all directions. As a result, as mentioned above, the artery of the wrist can be oppressed sufficiently.

(Embodiment 2)

A configuration of exemplary embodiment 2 on the basis of the above principle of oppression is explained by referring to FIG. 7 and FIG. 8. FIG. 7 shows only the air bags in a state before supply of air, and FIG. 8 shows a state after supply of air.

As shown in FIG. 7, the structure comprises a first air bag 14C as a first inflatable portion, and a second air bag 16C as a second inflatable portion positioned between the first air bag 14C and the wrist, being made of a material of a higher stretchability than the material of the first air bag 14C. Specific materials and thickness of the first air bag 14c are same as in embodiment 1. In structure, similarly, a taper is formed of side walls 14a, 14b for encouraging inflation to the wrist side. Specific materials for the second air bag 16C are also same as in embodiment 1, but the structural feature of this embodiment is that the shape of the second air bag 16C at the wrist side is an undulated shape 18.

By this undulated structure 18, as shown in FIG. 8, when air is supplied into the first air bag 14C and second air bag 16C, a higher stretchability than in embodiment 1 is obtained at the wrist side of the second air bag 16C, and when inflated, the second air bag 16C can intrude more securely into the tendons or bones. Or if the required size of the second air bag 16C in inflated state is same as in embodiment 1, in deflated state, the size of the second air bag 16C is smaller than in embodiment 1, so that the size of the air bag can be reduced.

FIG. 9 and FIG. 10 perspective development views showing the specific shape of the undulated shape 18 at the wrist 1 side of the second air bag 16C. FIG. 9 shows a first undulated shape 18A, in which (a) is a general perspective view, (b) is a sectional arrow view of X—X of (a), and (c) is a sectional view in inflated state. FIG. 10 is a general perspective view showing a second undulated shape 18B at the wrist 1 side of the second air bag 16C.

The undulated shape 18A in FIG. 9(a) comprises extruding portions 18a and dent portions 18b disposed alternately like waves along the longitudinal direction (see sectional view in FIG. 9(b)), and in inflated state, as shown in FIG. 9(c), all parts corresponding to the extruding portions 18a and dent portions 18b come to the outer side, so as to be inflated largely. The length of the extruding portions 18a is about 30 mm, the width is about 7.5 mm, and the height is about 2 mm.

On the other hand, the undulated shape 18B shown in FIG. 10 comprises block-shaped extruding portions 18a disposed in a matrix, and dent portions 18b disposed between the extruding portions 18a like a lattice. The size of one extruding portion 18a is about 7.5 mm×7.5 mm, and the height is about 2 mm. In the case of this undulated shape 18B, too, same as in the undulated shape 18A, when inflated, all parts corresponding to the extruding portions 18a and dent portions 18b come to the outer side, so as to be inflated largely.

In embodiments 1 and 2, the first air bags 14A, 14B, 14C, and second air bags 16A, 16B, 16C are provided in order to oppress both the radial artery 5 and ulnar artery 7 of the wrist, but a method of oppressing only the vicinity of the radial pedicular process is proposed by S. Mutsu et al. in "Analysis by finite element method about fitting position and size of cuff for local oppression in measurement of blood pressure by the wrist" (11th fall general meeting of Japan Society of ME). This paper, however shows or, teaches nothing about the technology of using first air bag and second air bag.

Therefore, the structure of these embodiments can be also applied in a structure for oppressing only the vicinity of the radial pedicular process. FIG. 11 shows the structure of the cuff 10 of a wrist-mount blood pressure monitor being applied for oppressing only the vicinity of the radial pedicular process. In this case, too, by inflation of the first air bag 14A, a specified pressure to the wrist 1 side is assured, and the second air bag 16A is inflated in a state of tight contact with the wrist 1, and the second air bag 16A intrudes flexibly into the tendons or bones, so that the second air bag 16A gets into the space between the radius 2 and palmar long flexor tendon 4b, so that the radial artery 5 can be sufficiently oppressed.

In the foregoing embodiments, the first air bag and second air bag are composed as independent air bags, but they may be made of a single air bag as far as the region of the first air bag is inflated mainly toward the wrist 1 side when air is supplied and the region of the second air bag is inflated to intrude mainly into the tendons or bones of the wrist 1 when air is supplied.

In the embodiments, air is used as the fluid, but not limited to air, but other gas having similar properties may be used (for example, oxygen, carbon dioxide, helium). Not limited to gas, water or other liquid may be also used. When liquid is used, an airtight structure must be employed in the fluid passage so as to avoid liquid leak.

Therefore, the present embodiments are illustrative and not restrictive, since the scope of the invention is defined by the appended claims rather than by the description preceding them, and all changes that fall within metes and bounds of the claims, or equivalence of such metes and bounds thereof are therefore intended to be embraced by the claims.

According to the cuff of a wrist-mount blood pressure monitor according to the invention, the pressure from the first inflatable portion is applied to the wrist which is kept in contact with the second inflatable portion regardless of the presence of tendons and bones of the wrist, and the artery of the wrist can be oppressed sufficiently. As a result, the problem of lack of oppression force of the artery is eliminated, and the blood pressure can be measured precisely by using a wrist-mount blood pressure monitor.

What is claimed is:

1. A cuff of a blood pressure monitor configured to be mounted on a wrist of a subject, comprising:

an inflatable bag for pressurizing an artery of the wrist, the inflatable bag receiving a fluid for inflation, the inflatable bag comprising a first inflatable portion and a second inflatable portion, the second inflatable portion being disposed between the first inflatable portion and the wrist, a material used to form the second inflatable portion having a lower elastic coefficient than a material used to form the first inflatable portion; and a mounting device for mounting the inflatable bag on the wrist, wherein the first and second inflatable portions are configured to expand under application of pressure substantially the same to the first and second inflatable portions.

2. The cuff of a blood pressure monitor of claim 1, wherein the first inflatable portion expands substantially toward the wrist when the first inflatable portion is inflated with the fluid, and the second inflatable portion extends so that a portion of the second inflatable portion intrudes into a space between a tendon, a muscle or a bone of the wrist when the second inflatable portion is inflated with the fluid.

3. The cuff of a blood pressure monitor of claim 1, wherein the material used to form the second inflatable portion is a silicone or a latex.

4. The cuff of a blood pressure monitor of claim 2, wherein the material used to form the second inflatable portion is a silicone or a latex.

5. The cuff of a blood pressure monitor of claim 1, 2, 3 or 4, wherein the second inflatable portion comprises a surface having a protruding portion and an indented portion, the surface of the second inflatable portion being configured to contact a surface of the wrist.

6. The cuff of a blood pressure monitor of claim 5, wherein the surface of the second inflatable portion further comprising a plurality of protruding portions and a plurality of indented portions, and the protruding portions and the indented portions are aligned at least in one direction of the surface.

7. The cuff of a blood pressure monitor of claim 1, wherein the fluid is air.

8. The cuff of a blood pressure monitor of claim 1, further comprising a conduit connected to the first inflatable portion and the second inflatable portion, the fluid being introduced to the first inflatable portion and the second inflatable portion through the conduit.

9. The cuff of a blood pressure monitor of claim 1, wherein the second inflatable portion is configured to expand more than the first inflatable portion under the application of the pressure.

* * * * *